United States Patent
Zhang et al.

(10) Patent No.: US 11,406,499 B2
(45) Date of Patent: Aug. 9, 2022

(54) EASY-TO-CONTROL INTERVENTIONAL INSTRUMENT DELIVERY DEVICE

(71) Applicant: VENUS MEDTECH (HANGZHOU), INC., Zhejiang (CN)

(72) Inventors: Zhifei Zhang, Hangzhou (CN); Zhenjun Zi, Hangzhou (CN); Min Frank Zeng, Irvine, CA (US); Quangang Gong, Hangzhou (CN)

(73) Assignee: Venus Medtech (Hangzhou) Inc., Hangzhou (CN)

( * ) Notice: Subject to any disclaimer, the term of this patent is extended or adjusted under 35 U.S.C. 154(b) by 0 days.

(21) Appl. No.: 16/856,440

(22) Filed: Apr. 23, 2020

(65) Prior Publication Data

US 2020/0315796 A1 Oct. 8, 2020

Related U.S. Application Data

(63) Continuation of application No. PCT/CN2018/111573, filed on Oct. 24, 2018.

(30) Foreign Application Priority Data

Oct. 24, 2017 (CN) .......................... 201710999545.1

(51) Int. Cl.
*A61F 2/24* (2006.01)
(52) U.S. Cl.
CPC ............ *A61F 2/2436* (2013.01); *A61F 2/243* (2013.01); *A61F 2/2418* (2013.01)
(58) Field of Classification Search
CPC ...... A61F 2/2436; A61F 2/2418; A61F 2/243; A61F 2/95; A61F 2/2439; A61F 2/966; A61M 25/0105; A61M 25/0133
See application file for complete search history.

(56) References Cited

U.S. PATENT DOCUMENTS

| 8,192,351 B2 | 6/2012 | Fishler et al. |
| 9,649,212 B2 | 5/2017 | Fargahi |

(Continued)

FOREIGN PATENT DOCUMENTS

| CN | 103190968 A | 7/2013 |
| WO | WO2010/005524 A2 | 1/2010 |

(Continued)

OTHER PUBLICATIONS

Office Action dated Jul. 12, 2021 for corresponding European Application No. 18871043.8.

*Primary Examiner* — Jerrah Edwards
*Assistant Examiner* — Mihret Tafesse
(74) *Attorney, Agent, or Firm* — Raymond Sun

(57) ABSTRACT

An easy-to-control interventional instrument delivery device, comprising a core tube (7), a guiding head (2) and a fixing head (3) being fixed onto the core tube (7); the guiding head (2) is fixed at a distal end of the core tube (7), and the fixing head (3) extends from a proximal end side of the core tube (7), an interventional instrument mounting position being located between the guiding head (2) and the fixing head (3); the outer periphery of the interventional instrument mounting position is provided with an axially skiable outer sheathing tube (5), further being provided with a floating limiting strip (1); a proximal end of the floating limiting strip (1) is a starting end (13) that is connected near the fixed head (3), and a distal end is a terminal end (11, 101) that floats between the interventional instrument mounting position and the outer sheathing tube (5). The easy-to-control interventional instrument delivery device is capable of fastening an end portion of a valve stent (8) during stent release so as to prevent the stent (8) from completely falling out during release, and reduces the relative friction between the delivery device and the valve during stent release and recovery.

16 Claims, 9 Drawing Sheets

(56) References Cited

U.S. PATENT DOCUMENTS

| | | | |
|---|---|---|---|
| 2010/0094411 A1* | 4/2010 | Tuval | A61F 2/2427 623/2.1 |
| 2012/0095542 A1* | 4/2012 | Tekulve | A61F 2/86 623/1.11 |
| 2017/0231765 A1* | 8/2017 | Desrosiers | A61F 2/2418 623/2.11 |
| 2020/0113719 A1 | 4/2020 | Desrosiers et al. | |

FOREIGN PATENT DOCUMENTS

| | | |
|---|---|---|
| WO | WO2010005524 A2 | 1/2010 |
| WO | WO2019/006332 A1 | 1/2019 |

\* cited by examiner

EASY-TO-CONTROL INTERVENTIONAL INSTRUMENT DELIVERY DEVICE

TECHNICAL FIELD

The present disclosure relates to the technical field of medical apparatuses, and in particular, to a delivery device for implanting an artificial heart valve into the heart.

BACKGROUND

Heart valve disease is one of the most common heart diseases in China, and the main symptom is valve damage caused by rheumatic fever. In recent years, with the development of the aging population, valve degeneration such as calcification and mucus degeneration, etc., and valve damage with metabolic disorder are also increasing in China. In addition, congenital valvular disease is also one of the common reasons for the heart disease. A considerable number of high-risk patients with heart valve disease, such as patients with severe valve insufficiency, elderly patients who are not suitable for surgical valve replacement, or patients with advanced tumors and valve insufficiency, require new and less invasive interventional treatment. Implantable heart valves were developed under the inspiration of surgical heart valve replacement. In recent years, percutaneous valve interventions have emerged and have been successfully applied to humans since 2000. From the stage of experimental research to the stage of small-scale clinical research, valve intervention breaks through the technical "bottleneck" and can be widely and quickly applied to the clinical practices, and becomes the focus of interventional cardiology again.

In the prior art, an artificial heart valve stent is compressed and delivered into the human body through a delivery device. The compressed valve stent is usually flexible, and when in a compressed configuration, it applies a great force to the compressing catheter. Due to the great force, it is difficult to gradually and precisely release the valve stent, resulting in excessive friction between the valve stent and the inner wall of the blood vessel.

CN patent No. 101953725 discloses an artificial heart valve stent, which includes an aortic stent, a valve stent, an outflow channel stent, and a connecting ear. When the heart valve is compressed into the delivery device, the connecting ear can be engaged in a fixing component of the delivery device for the stent. During the release of the valve stent, the valve stent is gradually released through the engagement of the connecting ear and the constraint of the outer sheath. However, in the prior art, the constraint force of the connecting ear of the valve stent is small, and the connecting ear can easily spring out of the fixing component of the delivery device for the stent at the end of the release of the valve stent, which causes the valve stent to be completely released. At this time, if problems such as positioning deviation occur, the valve stent cannot be retracted in time and can only be replaced by surgery.

In order to overcome the above-mentioned problems during the release of the valve stent in the human body, U.S. Pat. No. 5,683,451 discloses a delivery device and a method for controlling the release of a tubular prosthesis. The friction to the delivery catheter caused by a flexible expansion during delivery and release of the prosthesis is reduced by providing a rail in the delivery device. This invention reduces the friction between the prosthesis and the delivery catheter. However, the problem that the valve stent is suddenly and completely released due to an excessive expansion force during the release is not solved. The valve stent after being released into position cannot be adjusted or repositioned, which not only requires high control accuracy for surgery, but also contains certain risks.

SUMMARY

The present disclosure provides a delivery device for controlling the release of an implantable instrument, which can fix the end of the implantable instrument during the release of the implantable instrument, prevent the implantable instrument from getting out of control and falling off a fixing head during the release due to a great expansion force, and achieve repositioning and retrieval of the implantable instrument during the release.

A delivery device facilitating control of an implantable instrument comprising:

a core tube having a distal end and a proximal end, a guiding head which is fixed at the distal end of the core tube, a fixing head which is fixed on the core tube and is provided with at least one positioning portion on an outer wall thereof for engaging with at least one connecting ear of the implantable instrument, wherein the proximal end of the core tube extends through and out of the fixing head, with a mounting portion for the implantable instrument formed between the guiding head and the fixing head, an outer sheath which is configured for surrounding an outer periphery of the mounting portion for the implantable instrument and is slidable in an axial direction, and at least one movable limiting bar having a proximal end being a starting end which is fixed with the core tube or the fixing head, and a distal end being a terminal end which is configured between the mounting portion for the implantable instrument and the outer sheath and is movable, wherein, the at least one movable limiting bar is configured to maintain the engagement between the at least one connecting ear and the at least one positioning portion under the constraint of the outer sheath when the implantable instrument is in a loaded configuration.

In the present disclosure, the movable limiting bar is located between the outer sheath and the implantable instrument so that the inner wall of the outer sheath can radially constrain the implantable instrument and prevent the implantable instrument from getting out of control and falling off unexpectedly. Furthermore, the movable limiting bar can reduce the contact area between the outer sheath and the implantable instrument to a certain extent and reduce the friction therebetween, so that less force from an operator is required during pushing and withdrawing of the outer sheath so that the release and the retraction of the implantable instrument can be precisely controlled.

The mounting portion for the implantable instrument can be interpreted as a position where the implantable instrument is located when loaded. The main portion of the implantable instrument is located between the distal end of the fixing head and the proximal end of the guiding head. In general, for easy positioning, the implantable instrument is partially overlapped on the outer walls of the fixing head and the guiding head. Therefore, the position where the implantable instrument is located when loaded can be considered as an axial position between the distal end of the fixing head and the proximal end of the guiding head.

The movable limiting bar, without constraint of the outer sheath, can freely swing, or retain position and shape relative to the implantable instrument or the core tube only by utilizing the material strength thereof. The term of "movable" means that one end of the movable limiting bar is fixed, and the other end can swing at least in the radial direction without external constraint. Due to the material strength thereof, the movable limiting bar may displace in the circumferential direction.

The loaded configuration of the implantable instrument includes an unreleased configuration, in which the implantable instrument is completely surrounded by the outer sheath, and a partial released configuration, in which the implantable instrument is partially exposed out of the outer sheath. In the loaded configuration, the movable limiting bar maintains the engagement between the connecting ear of the implantable instrument and the positioning portion under the constraint of the outer sheath to prevent the connecting ear from falling off the fixing head.

The implantable instrument has a released configuration, in which the implantable instrument is completely exposed out of the outer sheath. In the released configuration, the force from the movable limiting bar to maintain the engagement between the connecting ear and the positioning portion is released so that the connecting ear of the implantable instrument is allowed to fall off the positioning portion.

In other words, the movable limiting bar maintains the engagement between the connecting ear of the implantable instrument and the positioning portion only in the loaded configuration.

The engagement structure of the implantable instrument with the positioning portion is generally configured as a connecting portion of the implantable instrument, and the connecting ear of the implantable instrument is at least a part of the connecting portion.

The positioning portion has an opening area, through which the radial position of the connecting ear can be changed. In the loaded configuration, the movable limiting bar blocks the opening area, and can completely or partially close the opening area.

The positioning portion has a radial opening area. During the release of the implantable instrument, the connecting ear falls off the positioning portion through the opening area. In the loaded configuration, the movable limiting bar blocks the opening area and prevents the connecting ear from falling off. In the unreleased configuration, the movable limiting bar completely or partially closes the opening area at the opening of the opening area on the outer periphery of the fixing head.

After the implantable instrument is loaded into the outer sheath, the movable limiting bar maintains the engagement between the connecting ear and the positioning portion under the constraint of the outer sheath. During the release of the connecting ear by withdrawing the outer sheath, the movable limiting bar is gradually released out of the outer sheath and it cannot freely swing until the connecting ear is completely released and falls off the fixing head. The released movable limiting bar would no longer apply radial pressing force to the connecting ear, and also would not constrain the connecting ear.

After the implantable instrument is loaded into the outer sheath, the movable limiting bar also serves as a spacer compensating the tolerance between the outer sheath and the connecting ear and filling the radial gap between the outer sheath and the connecting ear. The movable limiting bar has a simple structure and would not increase the radial size of the delivery device when implanted, and can enhance the engagement between the known implantable instrument and the fixing head to improve the connection therebetween. The radial force from the movable limiting bar to the connecting ear will be released with the withdrawal of the outer sheath so that the movable limiting bar would not obstruct the released valve stent.

The starting end of the movable limiting bar is fixed with at least one of the core tube and the fixing head.

The position of the fixing head relative to the core tube is fixed. The starting end of the movable limiting bar is fixed with at least one of the core tube and the fixing head. Alternatively, at least the axial position of the starting end of the movable limiting bar is fixed relative to at least one of the core tube and the fixing head.

The proximal end of the movable limiting bar is fixed using at least one of the following techniques:

a) the starting end of the movable limiting bar is fixed on the fixing head;

b) the starting end of the movable limiting bar is fixed on the core tube and located at the proximal end of the fixing head.

The proximal end of the movable limiting bar is fixed with the core tube or the fixing head, and the distal end of the movable limiting bar is movable relative to the core tube or the fixing head. For example, the starting end of the movable limiting bar is fixed, adjacent to the fixing head, or at the rear of the fixing head at the proximal end (the end adjacent to an operator in the direction of the delivery device), or at the core tube connected with the rear. Before operation, the outer sheath constrains the implantable instrument and the movable limiting bar and causes the movable limiting bar to radially and inwardly abut against the outer periphery of the implantable instrument. The movable limiting bar abutting against the outer periphery of the implantable instrument can be interpreted as the movable limiting bar only contacting with the outer periphery of the implantable instrument. In other words, the movable limiting bar does not extend into the radial inner side of the implantable instrument. During the release of the implantable instrument which has already been in the human body, the movable limiting bar turns outwardly with the withdrawal of the outer sheath and the release of the implantable instrument.

Without constraint of the outer sheath, the movable limiting bar changes its radial position by deforming partially or completely to allow the connecting ear to move radially and outwardly to fall off the positioning portion. At least a part of the movable limiting bar has a deformable structure that is made of flexible material and/or is formed as an articulated mechanism.

Preferably, the positioning portion is configured as a positioning protrusion, and when the implantable instrument assumes the loaded configuration, the connecting ear is configured to surround a respective positioning protrusion, and the movable limiting bar is configured to overlap and abut against an outer side of a respective connecting ear to maintain the engagement between the connecting ear and the positioning portion.

Preferably, the positioning portion is configured as a positioning groove, and when the implantable instrument assumes the loaded configuration, the connecting ear is configured to be inserted in a respective positioning groove, and the movable limiting bar is configured to overlap and abut against an outer side of a respective connecting ear to maintain the engagement between the connecting ear and the positioning portion.

In order to control the axial position of the implantable instrument, the proximal end of the implantable instrument is generally provided with a connecting ear for engaging with the fixing head. The connecting ear is generally T-shaped, L-shaped, ring-shaped, U-shaped, or V-shaped. The positioning portion may be a positioning groove for receiving the T-shaped or the L-shaped connecting ear, or may be a protrusion surrounded by the ring-shaped, the U-shaped, or the V-shaped connecting ear, for limiting the axial position of the implantable instrument in the loaded configuration. The shape of the connecting ear itself in the present disclosure may be known in the prior art, and is not the focus of the improvement for the present disclosure.

The portion of the movable limiting bar received in the positioning groove radially and inwardly contacts with or abuts against the connecting ear.

The positioning portion may be configured as a positioning protrusion or a positioning groove. In the loaded configuration, the connecting ear is surrounded around the respective positioning protrusion or inserted in the respective positioning groove.

In the loaded configuration, the movable limiting bar can maintain the engagement between the connecting ear and the positioning portion by directly overlapping and abutting against the connecting ear or blocking the positioning portion at the opening area.

The movable limiting bar overlapping and abutting against the connecting ear also means the movable limiting bar blocking the opening area, in which case, due to the limited radial gap, the movable limiting bar contacts with and presses against the connecting ear. In the case where the radial gap between the outer sheath and the positioning portion is larger, the movable limiting bar may not directly radially contact with the connecting ear, but locks the connecting ear by blocking the opening area. After the radial gap is filled by the movable limiting bar, the depth of the remaining gap should be less than the thickness of the connecting ear to prevent the connecting ear from falling off the positioning portion. In the loaded configuration, the radial outer side of the movable limiting bar abuts against the inner wall of the outer sheath, and the radial inner side of the movable limiting bar abuts against the connecting ear. Further, the movable limiting bar contacts with the implantable instrument at the radial outer side of the implantable instrument.

In the loaded configuration, the movable limiting bar is aligned with the outer wall of the fixing head in the radial direction, or protrudes from the outer wall of the fixing head in the radial direction.

In the loaded configuration, the movable limiting bar, under the constraint of the outer sheath, at least has a radial component to prevent the connecting ear of the implantable instrument from moving radially and outwardly, and to urge the connecting portion of the implantable instrument to abut against the fixing head.

The positioning protrusion or the positioning groove is the position of the positioning portion engaged with the connecting ear, which serves as a constraint structure for constraining the axial movement of the connecting ear in the loaded configuration, and allows the implantable instrument to move relative to the positioning portion in the released configuration to release the axial constraint.

In the loaded configuration, the portion of the movable limiting bar engaged with the positioning groove is radially received in the positioning groove in a partial or complete manner.

For example, in the case where a positioning groove is adopted, the connecting ear is latched in the positioning groove in the loaded configuration so as to achieve an axial positioning. After the outer sheath is withdrawn, the connecting ear falls off the positioning groove outwardly in the radial direction of the stent.

The positioning groove can be combined with a protrusion which may be provided at the bottom of the positioning groove and engages with the connecting ear in a form-fit manner to enhance the positioning.

In the case where the connecting ear has a U-shaped or an annular structure, one side of the U-shaped or the annular structure is connected with the implantable instrument. The positioning portion of the fixing head is configured as a positioning protrusion which engages with the U-shaped or the annular structure. The U-shaped or the annular structure can be extended around the positioning protrusion to achieve an axial positioning. In order to prevent the connecting ear from radially protruding too much, a recess is preferably provided around the outer periphery of the positioning protrusion, i.e., on the outer wall of the fixing head. The connecting ear is received in the recess, and the outer surface thereof is aligned with the outer wall of the fixing head in the radial direction.

Preferably, the number of the movable limiting bars is the same as that of the positioning grooves, and the movable limiting bars correspond to the positioning grooves respectively in a circumferential direction.

The positioning groove prevents the movable limiting bar from displacing during the retraction and release.

In the loaded configuration, the proximal end of the movable limiting bar under the constraint of the outer sheath is tightly latched in the positioning groove and presses against the connecting ear received in the positioning groove. During the release of the implantable instrument by withdrawing the outer sheath, the implantable instrument is prevented from getting out of control and falling off under the pressing and fixing of the movable limiting bar in the positioning groove. If the implantable instrument is released at an undesired position during release, the released implantable instrument can be compressed and retracted by pushing the outer sheath. At this time, the connecting ear is tightly surrounded by the movable limiting bar and the outer sheath, thereby ensuring a safe control for the implantable instrument and the repositioning.

Preferably, the terminal end of the movable limiting bar at least extends to the position corresponding to the connecting ear. In other words, the terminal end of the movable limiting bar at least extends to cover a part of the connecting ear to limit the radial movement of the connecting ear. The terminal end of the movable limiting bar may further extend towards the distal end and slidably engages with the outer sheath in the axial direction.

Preferably, the movable limiting bar is configured as a single strip, or a branched structure, wherein branches of the branched structure extend towards the distal end to overlap and abut against an outer side of the connecting ear, and a connection of the branched structure connecting the branches is fixed at an outer side of the fixing head.

The terminal end of the movable limiting bar is relative to the starting end and can also be interpreted as the distal end of the movable limiting bar.

Preferably, the most distal end of the movable limiting bar is aligned with the most distal end of the fixing head, or extends no more than the most distal end of the fixing head, or extends slightly beyond the most distal end of the fixing head.

In the case where the movable limiting bar has a minimum length, it should at least extend to cover the connecting ear. In order to further improve the pressing performance, the terminal end of the movable limiting bar may further extend to the distal end of the fixing head, or slightly beyond the distal end of the fixing head, such as by no more than 1 cm.

The distal end of the movable limiting bar extends to the portion of the implantable instrument having the greatest diameter. After a certain implantable instrument is released, the diameters of different portions of the implantable instrument may be different. In this case, the distal end of the movable limiting bar extends to the portion of the implantable instrument having the greatest diameter.

In the case where the movable limiting bar has a maximum length, the entire movable limiting bar should be able to be retracted in the outer sheath, and the terminal end of the movable limiting bar is aligned with the distal end of the implantable instrument in the outer sheath. In this case, the movable limiting bar is long enough to cover the overall implantable instrument. The movable limiting bar serves as a slide rail so that the outer sheath can be pushed and withdrawn without direct contacting with the implantable instrument.

In the loaded configuration of the implantable instrument, the movable limiting bar constrains the connecting ear in the positioning groove under the constraint of the outer sheath. The inner wall of the outer sheath contacts with the movable limiting bar and provides radial constraint. The movable limiting bar blocks the connecting ear in the positioning groove and prevents it from falling off.

Preferably, the positioning groove axially extends through the fixing head, and a portion of the movable limiting bar for engaging with the positioning groove is configured to be partially or completely received in the positioning groove.

The movable limiting bar extends through the positioning groove to the distal end. The positioning groove not only axially extends through the fixing head, but also is opened at the radial outer side thereof. In other words, the positioning groove has a radial opening. The movable limiting bar is not strictly required to be completely located at the inner side of the radial opening. A part of the movable limiting bar can be located at the outer side of the radial opening. For example, the movable limiting bar may have a T-shaped cross section. The bottom of the T-shaped structure may be located in the positioning groove to block the connecting ear, and the top of the T-shaped structure may be located at the outer side of the radial opening with a limited size in such a manner that the movable limiting bar can simultaneously engage with the inner side of the outer sheath and the connecting ear.

Preferably, an area of the positioning groove that axially extends through the fixing head is configured to be closed by the movable limiting bar.

In order to prevent the connecting ear from falling off, the width of the movable limiting ear may be equal to or slightly greater than the width of the radial opening of the area that axially extends through the fixing head so as to completely close the radial opening. Even if the width of the movable limiting ear may be smaller than the width of the radial opening, the gap formed therebetween should not be too large to allow the connecting ear to fall off. Preferably, the width of the movable limiting ear is equal to the width of the radial opening, which can further prevent the movable limiting ear from displacing.

Preferably, a portion of the movable limiting bar that is configured to be received in the positioning groove radially and inwardly contacts with or abuts against the connecting ear.

Even though the movable limiting bar can block the connecting ear, there may be a different relationship between the total thickness (a radial dimension) of the movable limiting bar and the connecting ear and the depth of the positioning groove. When the outer sheath covers and contacts with the outer periphery of the fixing head, the movable limiting bar overlaps the outer wall of the connecting ear. In the case where the total thickness of the movable limiting bar and the connecting ear is greater than the depth of the positioning groove, the movable limiting bar radially and inwardly abuts against the connecting ear. Conversely, the movable limiting bar only contacts with the connecting ear without a strong constraint force to the connecting ear. In any event, the movable limiting bar can constrain the connecting ear. Further preferably, the movable limiting bar abuts against the connecting ear so that the movable limiting bar can still constrain the connecting ear even if the axial force to the outer sheath is too large or the outer sheath is deformed.

Preferably, the movable limiting bar is configured to be aligned with or protrude from the outer wall of the fixing head in a radial direction.

The movable limiting bar at least extends radially and outwardly to the outer wall of the fixing head so that an undesired gap between the movable limiting bar and the inner wall of the outer sheath is avoided. The inner wall of the outer sheath abuts against the movable limiting bar and presses the connecting ear in the positioning portion of the fixing head.

Optionally, a portion of the movable limiting bar for engaging with the connecting ear extends in a straight line or a curved line.

In the case where the two sides of the movable limiting bar abut against the corresponding sides of the positioning groove, the movable limiting bar extending in the curved line can be appropriately narrowed so that it will be easy to turn outwardly to release the connecting ear during the release of the implantable instrument, thereby preventing the connecting ear from falling off with delay.

Optionally, the portion of the movable limiting bar for engaging with the connecting ear extends uniformly or non-uniformly in width.

The movable limiting bar has at least a portion that is overlapped with the positioning portion in the circumferential direction.

Optionally, the portion of the movable limiting bar for engaging with the connecting ear extends uniformly or non-uniformly in thickness. In the event that the portion of the movable limiting bar that engages with the connecting ear extends in a straight line or a curved line, it can be configured to extend uniformly or non-uniformly in width and/or in depth. The local strength of the movable limiting bar can be adjusted by changing the width or thickness so as to simultaneously ensure the constraint on the connecting ear and the release of the connecting ear.

Preferably, the terminal end of the movable limiting bar has a smooth outer periphery.

During operation, the movable limiting bar radially expands with the release of the implantable instrument. In order to prevent the terminal end of the expanding movable limiting bar from piercing the inner wall of the blood vessel, the terminal end of the movable limiting bar has a smooth outer profile, such as in the form of an approximate spherical crown or a chamfered edge.

Preferably, the movable limiting bars comprise two, three, or four movable limiting bars that are evenly arranged in a circumferential direction.

Preferably, the movable limiting bars have the same or different lengths.

In the case where the movable limiting bars have different lengths, the terminal ends of the movable limiting bars may be located at different positions. For example, at least one of the movable limiting bars extends to be aligned with the distal end of the fixing head, and at least one of the movable limiting bars extends to the distal end of the mounting portion for the implantable instrument.

There is a plurality of movable limiting bars which simultaneously or successively transform into the loaded configurations.

Preferably, there is a plurality of movable limiting bars which simultaneously or successively transform from the loaded configurations into the released configurations.

The loaded configuration can be interpreted as the movable limiting bars are completely surrounded by the outer sheath, and the released configuration can be interpreted as the movable limiting bars are completely exposed out of the outer sheath. In the case where the distal ends of the movable limiting bars are located at different axial positions, the movable limiting bars successively transform into the loaded configurations. In the case where the distal ends of the movable limiting bars are located at the same axial position, the movable limiting bars simultaneously transform into the loaded configurations, which also means that the movable limiting bars simultaneously transform from the loaded configurations into the released configurations.

Preferably, there are three movable limiting bars with the same length which are configured as long strips.

Preferably, the movable limiting bar has a hollow or a solid structure.

Preferably, the movable limiting bar is configured as a flat strip with a solid structure.

The movable limiting bar configured as a flat strip occupies a small space in the radial direction of the mounting portion for the implantable instrument, which functions to reduce the outer diameter of the compressed delivery device.

Preferably, the movable limiting bar has a length of 10 mm to 80 mm, a width of 1 mm to 2 mm, and a thickness of 0.2 mm to 0.5 mm.

Preferably, the movable limiting bar is fixed with a connected part such as the core tube or the fixing head in a bonding, tying, latching, welding, or one-piece manner.

The movable limiting bar comprises a starting end at one end thereof, an extending section at the middle portion thereof, and a terminal end at the other end thereof. The starting end of the movable limiting bar is located, at the rear of the fixing head at the proximal end thereof, or at a portion of the core tube that connects the rear of the fixing head and an inner sheath. The starting end of the movable limiting bar is fixed with the connected part in a bonding, tying, latching, welding, or one-piece manner. The movable limiting bar extends from the starting end to the distal end. In a released configuration, the starting end of the movable limiting bar is fixed, and the extending section and the terminal end expand in the axial direction of the core tube.

Preferably, at least one of a portion of the movable limiting bar for engaging with the sheath and a portion of the movable limiting bar for engaging with the implantable instrument has a smooth surface and/or a lubricious coating.

Preferably, the movable limiting bar is made of PTFE material.

Preferably, the delivery device further comprises at least one fixing and guiding bar that is provided at an inner wall of the sheath and extends in the axial direction.

One side of the fixing and guiding bar is fixed in the tubular housing of the outer sheath at the distal end (in the direction of the delivery device away from an operator). The fixing and guiding bar extends in the axial direction of the tubular housing. When the implantable instrument is retracted and released by the outer sheath, the implantable instrument directly contacts with the fixing and guiding bar located in the tubular housing of the outer sheath, and it can be controlled quickly and precisely through the smooth rail provided by the fixing and guiding bar.

The fixing and guiding bar can be fixed to the inner wall of the outer sheath only at the contact portion therebetween, or at a plurality of fixing points spaced from each other, or be entirely fixed to the inner wall of the outer sheath. Since the fixing and guiding bar is required to move back and forth with the outer sheath, preferably at least the two axial ends of the fixing and guiding bar are fixed with the inner wall of the outer sheath to avoid a space interference caused by the evagination of the fixing and guiding bar.

Before operation, the outer sheath constrains the implantable instrument, and the fixing and guiding head abuts against the implantable instrument. During the subsequent release of the implantable instrument, the side of the fixing and guiding bar adjacent to the implantable instrument provides a smooth rail between the tubular housing of the outer sheath and the implantable instrument, which reduces the friction therebetween and facilitates the control and the release of the implantable instrument.

Preferably, the movable limiting bars and the fixing and guiding bars are arranged alternatively in a circumferential direction.

The positioning grooves of the fixing head and the fixing and guiding bars are arranged alternatively, which also means that the movable limiting bars and the fixing and guiding bars are arranged alternatively.

Preferably, the terminal end of the movable limiting bar and a distal end of the fixing and guiding bar are aligned with or offset from each other in an axial direction.

Preferably, there are two, three, or four fixing and guiding bars that are evenly arranged in a circumferential direction.

Preferably, the fixing and guiding bars have the same or different lengths.

Preferably, there are three fixing and guiding bars with the same length which are configured as long strips.

Preferably, the fixing and guiding bar has a hollow or a solid structure.

Preferably, the fixing and guiding bar is configured as a flat strip with a solid structure.

The fixing and guiding bar configured as a flat strip occupies a small space in the radial direction of the mounting portion for the implantable instrument, which functions to reduce the outer diameter of the compressed delivery device.

Preferably, the fixing and guiding bar has a length of 10 mm to 80 mm, a width of 1 mm to 2 mm, and a thickness of 0.2 mm to 0.5 mm.

Preferably, the fixing and guiding bar has a length of 60 mm to 80 mm.

The shape and size of the movable limiting bar and the fixing and guiding bar are independently provided. For example, they can be configured as long strips with solid or hollow structures. Preferably, the cross sections of the movable limiting bar and the fixing and guiding bar are flat. In order to reduce the radial size of the entire distal end of the outer sheath, the thickness direction of the flat structure corresponds to the radial direction of the outer sheath.

In order to control the release and the retraction of the stent well, the movable limiting bar and the fixing and guiding bar are configured with appropriate sizes to reduce the contact area between the stent and the outer sheath, thereby reducing the friction therebetween.

Preferably, the fixing and guiding bar is fixed with the inner wall of the sheath in a bonding, tying, latching, welding, or one-piece manner.

Preferably, a portion of the fixing and guiding bar for engaging with the implantable instrument has a smooth surface and/or a lubricious coating.

Preferably, the fixing and guiding bar is made of PTFE material.

In the present disclosure, the material of the movable limiting bar and the fixing and guiding bar are independently provided. Preferably, the movable limiting bar and the fixing and guiding bar are made of a biocompatible material with good flexibility. The specific material may be a known material.

Preferably, the implantable instrument is configured as a heart valve. Depending on the application, the implantable instrument can be a vascular stent.

In order to ensure that the movable limiting bars and the movable limiting bars have an appropriate flexibility and a small dynamic friction factor, the movable limiting bars and the movable limiting bars are preferably made of PTFE material. More preferably, the outer surfaces of the movable limiting bars and the movable limiting bars should be smooth enough. Alternatively, the outer surfaces of the movable limiting bars and the movable limiting bars may be provided with lubricious coatings. The lubricious coating may be made of hydrophilic monomer or polymer with lubricating property, such as N,N-dimethylacryl (DMAA), acrylamide (AAm), N-vinylpyrrolidone (NVP), Polyvinyl alcohol (PVA), polyacrylamide (PAAm), polyethylene glycol (PEG), etc. The coating may be coated on the outer surfaces of the movable limiting bars and the movable limiting bars using coupling agent or chemical technique.

DESCRIPTION OF THE EMBODIMENTS

The technical solutions according to the embodiments of the present disclosure will be described apparently and fully in combination with the drawings according to the embodiments of the present disclosure. Obviously, the described embodiments are only some of the embodiments of the present disclosure, but not all the embodiments. Based on the embodiments of the present disclosure, all other embodiments obtained by a person skilled in the art without creative efforts fall within the scope claimed by the present disclosure.

In order to better describe and illustrate the embodiments of the present disclosure, one or more drawings may be referred. However, additional details or illustrations for describing the drawings should not be regarded as limitations to the scope, to the embodiments of the present disclosure, or to the preferred developments described here.

It should be noted that, when a component is "connected" with another component, it may be directly connected to another component or may be indirectly connected to another component through a further component. Similarly, when a component is "provided" on another component, it may be directly provided on another component or may be provided on another component through a further component.

Unless otherwise defined, all technical and scientific terms used herein have the same meaning as commonly understood by a person skilled in the art. The terms in the description of the present disclosure are used to describe specific embodiments, and not to limit the present disclosure.

A proximal end herein refers to an end adjacent to an operator along the direction of a delivery device, and a distal end refers to an end away from the operator along the direction of the delivery device. In the embodiments, a valve stent is shown as an example of an implantable instrument.

Figure 1:
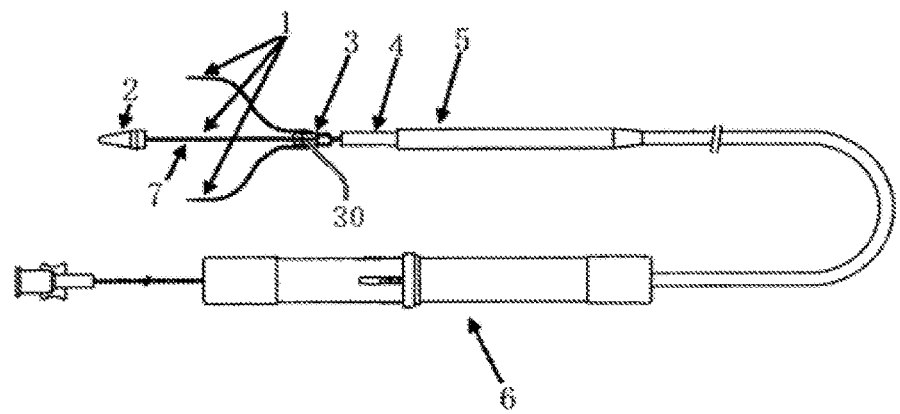
FIG. 1 is a schematic structural view of a delivery device for an implantable instrument according to an embodiment of the present disclosure.
Figure 2:
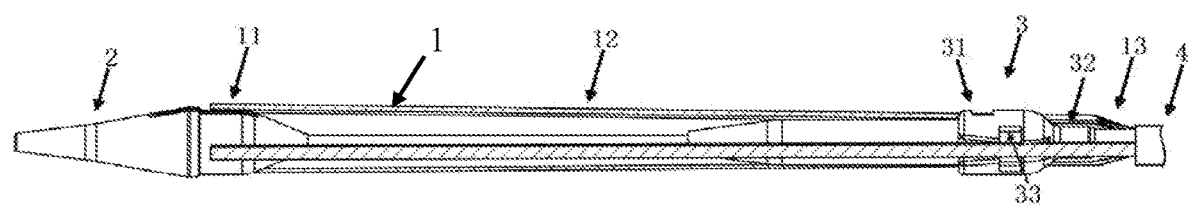
FIG. 2 is a schematic structural view of the distal end of the delivery device for the implantable instrument according to the embodiment of the present disclosure.

Referring to FIGS. 1 and 2, a delivery device for an implantable instrument according to the present disclosure includes a guiding head 2, a core tube 7, a movable limiting bar 1, a fixing head 3, an inner sheath 4, an outer sheath 5 and an operating handle 6, wherein the movable limiting bar 1 includes a starting end 13 at a proximal end thereof, an extending section 12, and a terminal end 11 at a distal end thereof.

Both the guiding head 2 and the fixing head 3 are fixed on the core tube 7, wherein the guiding head 2 is located at the most distal end of the core tube 7, and the fixing head 3 surrounds a section of the core tube 7 at the distal end thereof, with a mounting portion for the implantable instrument formed between the guiding head 2 and the fixing head 3. The fixing head 3 is provided with a positioning portion 30 on an outer wall thereof for engaging with a connecting ear of the implantable instrument. The connecting ear 81 of the implantable instrument is at least a part of an engagement structure for connecting the implantable instrument and the positioning portion 30. The outer sheath 5 is configured for surrounding an outer periphery of the mounting portion for the implantable instrument and is slidable in an axial direction. Both the proximal end of the core tube 7 and the proximal end of the outer sheath 5 are connected with the operating handle 6, and the outer sheath 5 is slidable in the axial direction relative to the core tube 7 by means of the operating handle 6. Depending on the application, the inner sheath 4 may be provided or may be omitted. In the case of providing the inner sheath 4, the inner sheath 4 surrounds the core tube 7 and is located at a proximal end of the fixing head 3, and in general, the inner sheath 4 does not move axially together with the outer sheath 5.

The core tube 7 may be formed in one piece. Alternatively, the core tube 7 may be formed by two sections which are inserted one in the other and thus connected with each other, and the joint portion is preferably located in the fixing head 3 so as to ensure sufficient joint strength and smooth profile of the core tube 7.

There are three movable limiting bars shown in FIG. 1 with the same length, each of which assumes a released configuration and freely extends without the constraint of the outer sheath.

Referring to FIG. 2, depending on the locations, the movable limiting bar 1 includes the starting end 13, the extending section 12, and the terminal end 11, wherein the starting end 13 is the proximal end of the movable limiting bar 1. The starting end 13 is fixed on the core tube 7 and located at a proximal end of the rear of the fixing head 32. It can be seen from FIG. 2 that the starting end 13 is located between the inner sheath 4 and the rear of the fixing head 32. The positioning portion in the present embodiment is configured as a positioning groove. The fixing head 3 is provided with at least one positioning groove 33 on the outer periphery thereof. As the positioning groove needs to engage with the connecting ear of the implantable instrument, both the location and the shape of the positioning groove should be suitable to the connecting ear. There are three positioning grooves provided on the fixing head 3 shown in FIG. 2, which are offset from each other in the axial direction. For example, the positioning grooves 31 and 33 shown in FIG. 2 are offset from each other in the axial direction. In order to allow the movable limiting bar 1 to freely extend, preferably, the at least one positioning groove axially extends through the fixing head 3. Since the connecting ear is configured to expand radially and outwardly and thus fall off the positioning groove during the release of the valve stent, the positioning groove opens radially and outwardly. In other words, the positioning groove includes a radial opening area. In a loaded configuration of the valve stent, the movable limiting bar 1 blocks at the radial opening area of the positioning portion 30, and closes the radial opening area in a complete or partial manner to prevent the connecting ear 81 from expanding radially and outwardly and thus falling off the positioning portion (i.e., the positioning groove 33 in the present embodiment).

The positioning groove in FIG. 2 includes an axial extending area through the fixing head 3 and two branched areas extending from two sides of the axial extending area respectively, which fits the T-shaped connecting ear in a form-fit manner. The movable limiting bar 1 extends through the axial extending area of the positioning groove to a distal end of the mounting portion for the implantable instrument. The movable limiting bar 1 shown in FIG. 2 assumes an unloaded configuration, and the terminal end 11 axially extends to an outer periphery of the guiding head 2.

As shown in FIG. 2, when the movable limiting bar 1 extends axially and straight, the distal end of the movable limiting bar 1 extends to the guiding head 2. When cooperating with the implantable instrument, the movable limiting bar 1 can also serve as a slide rail between the implantable instrument and the outer sheath, and function to guide. Preferably, without constraint from the outer sheath, the distal end of the movable limiting bar 1 expands and turns radially and outwardly, as shown in FIG. 1, so as to ensure the release of the implantable instrument, and to reduce unexpected radial obstruction from the movable limiting bar 1. The movable limiting bar 1 may be preset and expands radially and outwardly when the outer sheath is released. Alternatively, at least a part of the movable limiting bar 1 has a deformable structure that is made of flexible material and/or is formed as an articulated mechanism.

The starting end of the movable limiting bar 1 may be fixed with other parts by bonding, binding, locking, or welding, or may be formed in one piece with other parts. A biocompatible and anticorrosion adhesive is preferred as the material for bonding. A flexible and corrosion-resistant binding wire is preferred as the material for binding.

Figure 3:
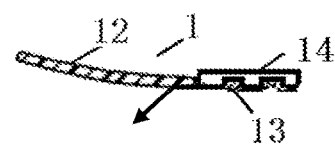
FIG. 3 is a schematic structural view of a locker.

In the case of welding, a locker made of alloy material may be connected to the rear of the fixing head or the core tube, and then the starting end of the movable limiting bar 1 may be tightly locked by the locker. As shown in FIG. 3 which only shows a part of the extending section 12, the starting end 13 of the movable limiting bar 1 is locked in the locker 14 that is made of stainless steel (316 stainless steel material). The locker 14 is connected on the fixing head 3 or the core tube 7 by welding.

Within the delivery device, as shown in FIGS. 1 and 2 in which the implantable instrument such as an implantable heart valve is not shown, the movable limiting bar 1 assumes the unloaded configuration. After the implantable instrument is loaded, the movable limiting bar 1 transforms into a loaded configuration in which the movable limiting bar 1 applies force to a connecting portion of the implantable instrument under the constraint of the outer sheath. For example, the movable limiting bar 1 can prevent the connecting ear of the implantable heart valve from falling off the positioning groove. The movable limiting bar also has a released configuration, in which the implantable instrument falls off the outer sheath and the movable limiting bar starts to release, and the applied force from the outer sheath through the movable limiting bar to the connecting portion of the implantable instrument is released. For example, when the outer sheath is withdrawn and the implantable heart valve is released, the force from the outer sheath through the movable limiting bar to the connecting ear of the implantable heart valve is released, and in the meantime, the valve stent radially expands and the connecting ear falls off the positioning groove.

Figure 4:
FIG. 4 is a schematic structural view of a distal end of a movable limiting bar.

The movable limiting bar 1 may be configured as a long strip with a solid or hollow structure. In the present embodiment, the movable limiting bar 1 is configured as a flat strip with a solid structure. As shown in FIG. 4, the terminal end 11 of the movable limiting bar 1 may be configured as an arc-shaped structure instead of a structure with sharp corners.

Each movable limiting bar 1 has a length of 10 mm to 80 mm, a width of 1 mm to 2 mm, and a thickness of 0.2 mm to 0.5 mm. In the case where the movable limiting bar 1 has a maximum length, the entire movable limiting bar 1 should be able to be received in the outer sheath 5, and the terminal end of the movable limiting bar 1 extends to the distal end of the valve stent 8. In the loaded configuration, the movable limiting bar 1 should be long enough to cover the entire valve stent 8 so that the outer sheath 5 may be pushed and withdrawn without direct contacting with the valve stent 8.

Referring to FIGS. 5A to 5D, in order to ensure that the movable limiting bar 1 has a small dynamic friction factor, the movable limiting bar 1 is preferably made of PTFE material. Each movable limiting bar 1 shown in FIGS. 5A to 5D has a length of 65 mm, a width adapted to be suited to the width of the positioning groove of the fixing head 3, and a thickness of 0.5 mm. When the movable limiting bars are in a constrained condition, three movable limiting bars axially extend through respective positioning grooves and further to the distal ends thereof, respectively. The valve stent 8 includes three T-shaped connecting ears. In order to fit the shape of the connecting ear, the positioning groove axially extends through the fixing head 3 and forms as a cross groove. In order to ensure the constraint effect, the axial extending area of the positioning groove is completely closed by a respective movable limiting bar 1. In other words, the width of the movable limiting bar 1 corresponds to the width of the axial extending area. In the case where the axial extending area axially extends with unequal widths at different positions, the width of the movable limiting bar 1 should at least correspond to the narrowest area of the axial extending area to ensure that the movable limiting bar 1 can be partially or completely received in the positioning groove. The outer surface of the movable limiting bar 1 may slightly protrude from the outer periphery of the fixing head 3 to reduce friction between the outer periphery of the fixing head 3 and the inner wall of the outer sheath 5.

Figure 5A:
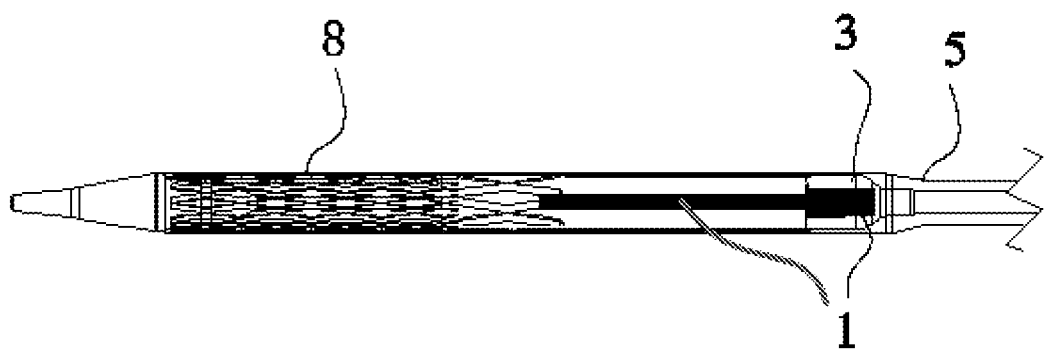
FIG. 5A shows a schematic structural view of the implantable instrument in an unreleased configuration which is completely surrounded by an outer sheath.
Figure 5B:
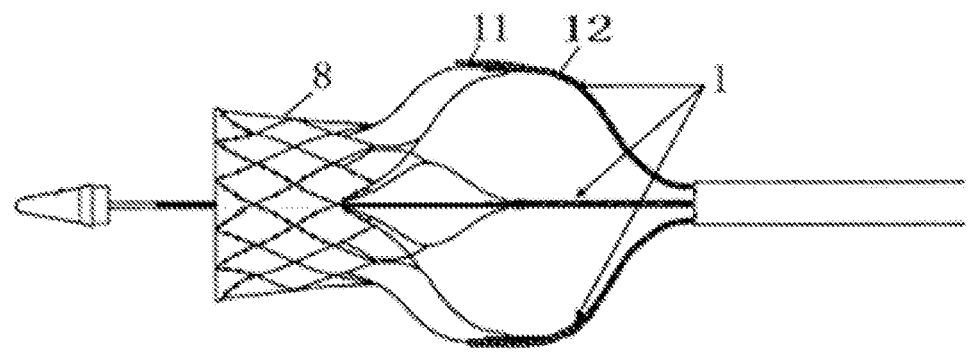
FIG. 5B shows a schematic structural view of the implantable instrument in a partial released configuration which is partially exposed out of the outer sheath.
Figure 5C:
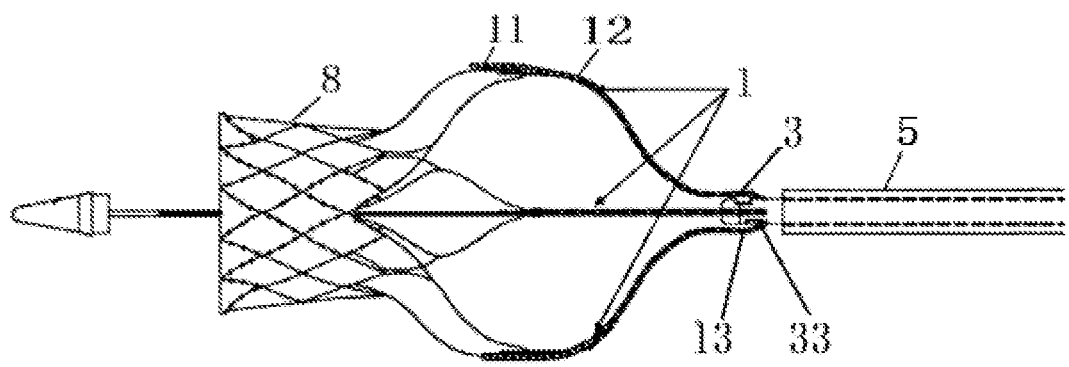
FIG. 5C shows a schematic structural view of the implantable instrument in a released configuration which is completely exposed out of the outer sheath, and the proximal end of the implantable instrument has not radially sprung out yet.
Figure 5D:
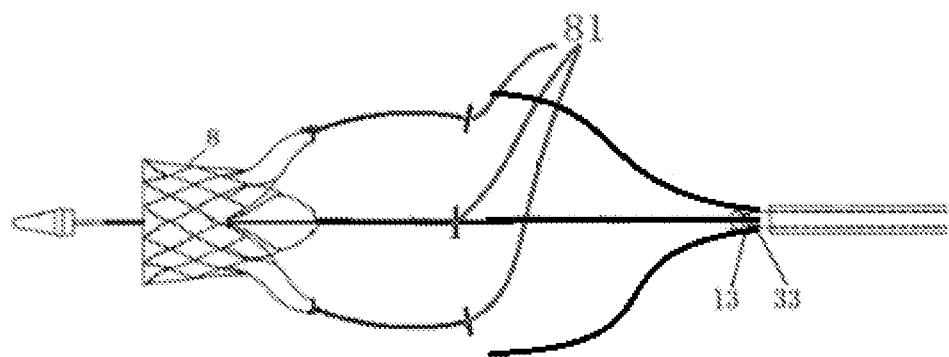
FIG. 5D shows a schematic structural view of the implantable instrument in a released configuration, and the proximal end of the implantable instrument has already radially sprung out.

FIGS. 5A and 5B show loaded configurations of the implantable instrument. FIG. 5A shows a loaded configuration of the implantable instrument 8 before being released, which is completely surrounded by the outer sheath 5. FIG. 5B shows a loaded configuration of the implantable instrument 8 being partially released and exposed. FIGS. 5C and 5D show released configurations of the implantable instrument. FIG. 5C shows a released configuration of the valve stent which is completely exposed out of the outer sheath 5, and the proximal end of which is self-expanded and has not sprung out yet, and this configuration is a momentary configuration which appears and disappears very quickly. FIG. 5D shows a released configuration of the valve stent in which the proximal end of the valve stent has already sprung out completely. In the loaded configuration of the implantable instrument, the movable limiting bar 1 prevents the connecting ear from falling off the positioning portion.

As shown in FIG. 5A, when the valve stent 8 is loaded into the delivery device, the movable limiting bar 1 starts to surround the valve stent 8 from the fixing head 3 to receive the valve stent 8 in the outer sheath 5. In the loaded configuration of the implantable instrument, the radial outer side of the movable limiting bar 1 abuts against the inner wall of the outer sheath, and the radial inner side of the movable limiting bar 1 limits the displacement of the connecting ear 81 from radially falling off the positioning groove.

As shown in FIG. 5B, during the release of the valve stent 8, the outer sheath 5 is withdrawn and slides along the movable limiting bar 1, thereby avoiding direct contacting with the valve stent 8. The terminal end 11 and the extending section 12 of the movable limiting bar 1 expand together with the valve stent, and during the gradual release of the valve stent, the terminal end 11 of the movable limiting bar 1 transforms from a configuration abutting against the valve stent 8 to an unfolded configuration. The outer sheath 5 is subsequently and gradually withdrawn along the movable limiting bar 1 until the valve stent 8 is completely released. As the starting end 13 of the movable limiting bar 1 is fixed on the fixing head 3, the extending section 12 of the movable limiting bar 1 adjacent to the starting end 13 experiences a constraint force from the starting end 13. In the case where the connecting ear of the valve stent 8 is inserted in the positioning groove 33 of the fixing head 3, the extending section of the movable limiting bar 1 adjacent to the proximal end thereof abuts against the positioning groove 33, and radially and inwardly presses against the connecting ear of the valve stent 8, thereby preventing the connecting ear from prematurely falling off the positioning groove 33 of the fixing head 3 during the release of the valve stent 8, thereby avoiding a sudden release of the valve stent 8. During the release of the valve stent 8, if the valve stent is placed at an unexpected position and needs to be replaced, because of the constraint force from the movable limiting bar 1 to the connecting ear in the positioning groove 3, it is possible to push the outer sheath 5 along the movable limiting bar 1 to fold the released portion of the valve stent 8 and thus withdraw the valve stent 8.

As shown in FIG. 5C, the outer sheath 5 is offset from a projection of the proximal end of the positioning groove 33 of the fixing head 3 on an axis of the outer sheath. The movable limiting bar 1 is no longer constrained by the outer sheath and does not limit the radial displacement of the connecting ear of the valve stent, which means that the constraint force from the movable limiting bar 1 to the connecting ear of the valve stent 8 is released. In other words, the movable limiting bar 1 transforms into the released configuration and the valve stent 8 is allowed to expand and fall off the positioning groove 33. The connecting ear shown in FIG. 5C has not radially sprung out yet, but is ready to radially spring out.

As shown in FIG. 5D, the connecting ear 81 of valve stent at the proximal end thereof has radially sprung out, and the movable limiting bar 1 is separated from the connecting ear.

Figure 6:
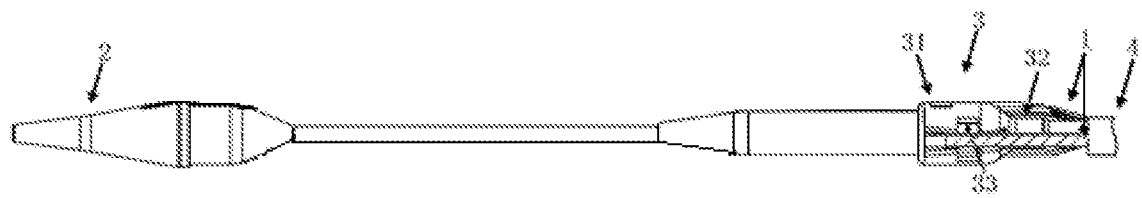
FIG. 6 is a schematic structural view of a delivery device for an implantable instrument with short movable limiting bars according to another embodiment of the present disclosure.

Referring to FIG. 6, in another embodiment, the movable limiting bar 1 has a short axial length, and the terminal end thereof is aligned with the distal end of the fixing head 3.

The movable limiting bar 1, shown in FIGS. 1, 2 and 5A to 5D, has a large size, which not only constrains the implantable instrument, for example, by limiting the radial displacement of the connecting ear of the heart valve stent and thus stabilizing the engagement between the connecting ear and the positioning portion, but also provides a smooth rail between the valve stent 8 and the outer sheath 5 to reduce the friction therebetween. As the outer sheath 5 directly contacts the movable limiting bar 1, less force from an operator is required during pushing or withdrawing of the outer sheath 5 so as to precisely control the release and the retraction of the valve stent 8.

Three movable limiting bars are shown in FIG. 6 which are configured as long strips with solid structures and are made of PTFE material. The starting end of the movable limiting bar 1 is fixed to the rear of the fixing head 3 at the proximal end thereof by bonding, and the terminal end of the movable limiting bar 1 is aligned with the distal end of the fixing head 3. In other words, the movable limiting bar 1 should at least completely cover the respective connecting ear and constrain it in the positioning groove. The width of the movable limiting bar 1 corresponds to the width of the axial extending area of the positioning groove 33. The movable limiting bar 1 has a thickness of 0.5 mm.

Referring to FIGS. 7A to 7E, in a further embodiment, the implantable instrument 8 has an unreleased configuration which is completely surrounded by the outer sheath 5, a partial released configuration which is partially exposed out of the outer sheath 5, and a released configuration which is completely exposed out of the outer sheath 5, wherein when the implantable instrument 8 is in either an unreleased configuration or a partial released configuration, each movable limiting bar is in a loaded configuration.

In this embodiment, the valve stent 8 is provided with connecting ears. After the valve stent 8 is loaded into the delivery device, the movable limiting bar 1 extends to a position where the distal end of the movable limiting bar 1 is aligned with the distal end of the fixing head 3, and the terminal end of the movable limiting bar 1 is only capable of abutting against the connecting ear which is inserted in the positioning groove 33 of the fixing head. After the valve stent 8 is delivered into the human body, it will be gradually released by withdrawing the outer sheath 5. In the meantime, the connecting ear 81 of the valve stent 8, which has already been inserted in the positioning groove 33 of the fixing head, will be firmly constrained in the positioning groove 33 under the constraint of the starting end of the movable limiting bar 1, thereby preventing the stent from being completely released in advance under the influence of the expansion force from the released portion of the valve stent 8 to the connecting ear.

The movable limiting bar 1 with small size avoids influence to the normal release of the stent and undesired constraint to the stent. The movable limiting bar 1 may also extend to the axial middle area of the valve stent 8. For example, the movable limiting bar 1 may extend no more than the axial largest area of the valve stent which has already been completely released, such as the area indicated by the point A shown in FIG. 7H.

Figure 7A:
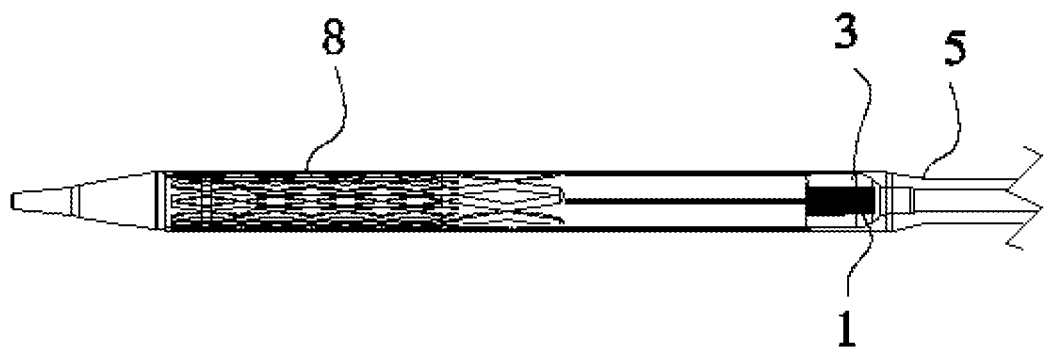
FIG. 7A shows a schematic structural view of an implantable instrument in an unreleased configuration according to a further embodiment of the present disclosure, in which the delivery device is provided with short movable limiting bars.

FIG. 7A shows the outer sheath 5, in which the valve stent 8 is in the unreleased configuration.

Figure 7B:
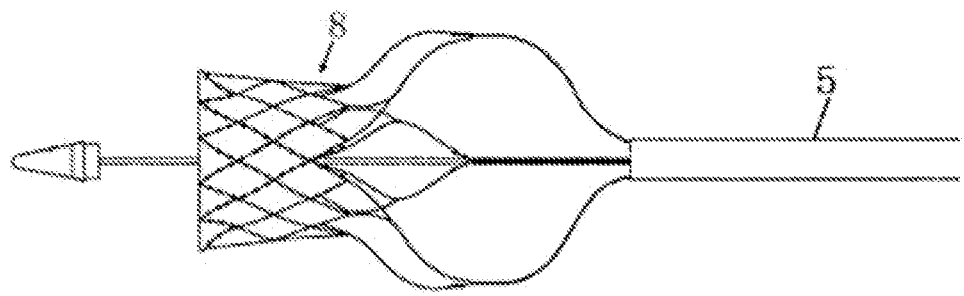
FIG. 7B shows a schematic structural view of the implantable instrument in a partial released configuration.

Referring to FIG. 7B, after the valve stent 8 is delivered into the human body, it will be gradually released by withdrawing the outer sheath 5. In the meantime, the connecting ear 81 of the valve stent 8, which has already been inserted in the positioning groove 33 of the fixing head, will be firmly constrained in the positioning groove 33 under the constraint of the starting end of the movable limiting bar 1, thereby preventing the stent from being completely released in advance under the influence of the expansion force from the released portion of the valve stent 8 to the connecting ear.

Figure 7C:
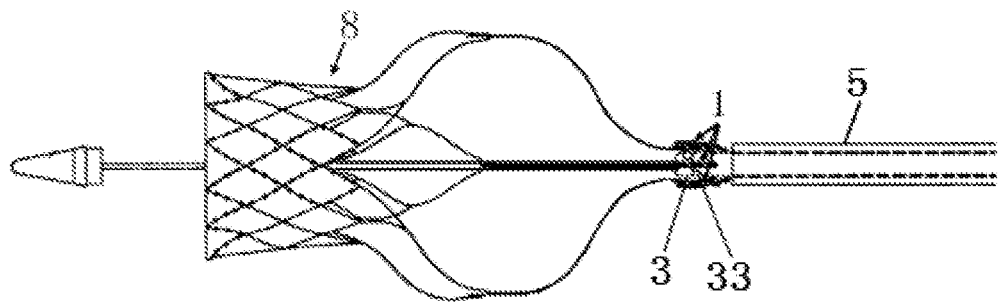
FIG. 7C shows a schematic structural view of the implantable instrument in a released configuration, in which the proximal end of the implantable instrument has not radially sprung out yet, and the delivery device is provided with short movable limiting bars.

Referring to FIG. 7C, after the outer sheath 5 is withdrawn, the outer sheath 5 is offset from a projection of the positioning groove 33 on an axis of the outer sheath. The movable limiting bar 1 is no longer constrained by the outer sheath, which means that the constraint force from the movable limiting bar 1 to the valve stent 8 is released. In other words, the movable limiting bar 1 is in the released configuration and the valve stent 8 is allowed to expand and fall off the positioning groove 33. The configuration shown in FIG. 7C is a momentary configuration which appears and disappears very quickly, and the connecting ear has not radially sprung out yet, but is ready to radially spring out.

The loaded configuration in the present disclosure refers to the configuration in which the connecting portion of the implantable instrument is engaged with the positioning portion. In particular, the loaded configuration may refer to the configuration in which the implantable instrument is assembled into the positioning portion. The released configuration refers to the configuration in which the connecting portion of the implantable instrument is allowed to fall off the positioning portion. It should be noted that the released configuration does not refer to the configuration in which the implantable instrument has already been completely released, but refer to the configuration in which the engagement between the connecting portion and the positioning portion is releasable. As to the remaining portion of the implantable instrument that is not configured for engaging with the positioning portion, it may have already been partially or completely released and expanded radially in the released configuration.

Figure 7D:
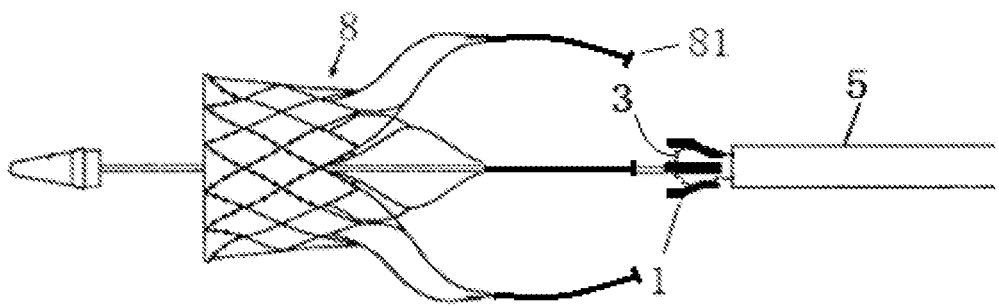
FIG. 7D shows a schematic structural view of the implantable instrument in a released configuration, and the proximal end of the implantable instrument has already radially sprung out.
Figure 7E:
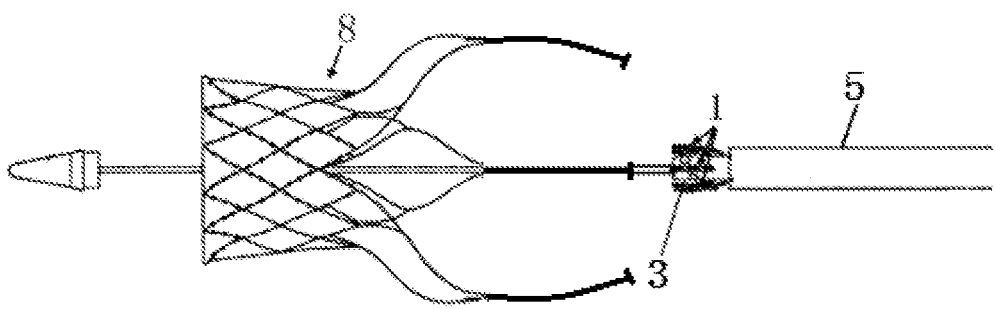
FIG. 7E shows a schematic structural view of the movable limiting bars shown in FIG. 7D which have already returned to position.

Referring to FIG. 7D, the connecting ear 81 pushes the movable limiting bar 1 that is radially deformable to radially spring out, and the movable limiting bar 1 subsequently turns outwardly. Referring to FIG. 7E, the movable limiting bars return to and contact with the fixing head 3.

Figure 7F:
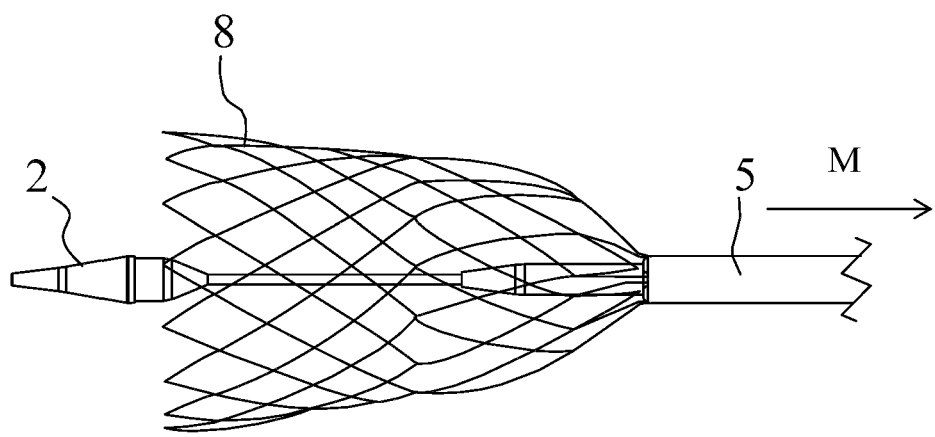
FIG. 7F shows a schematic structural view of an implantable instrument in a partial released configuration.
Figure 7G:
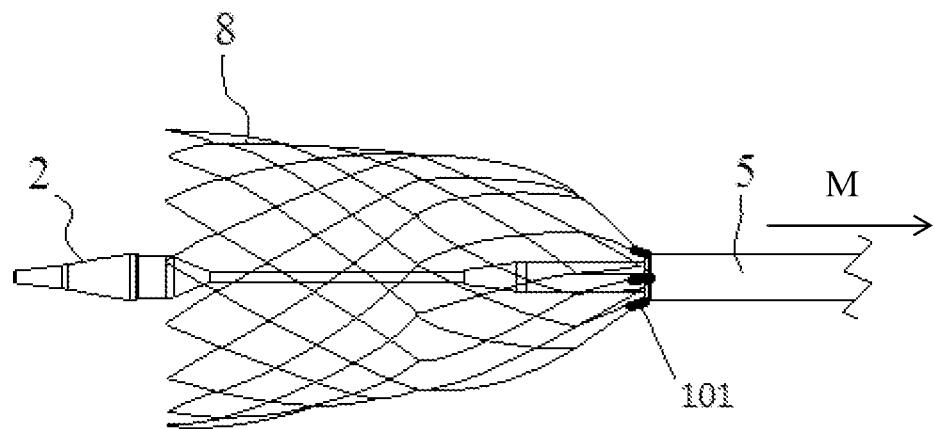
FIG. 7G shows a schematic structural view of a heart valve stent, in which the movable limiting bars are partially released during the release of the heart valve stent.
Figure 7H:
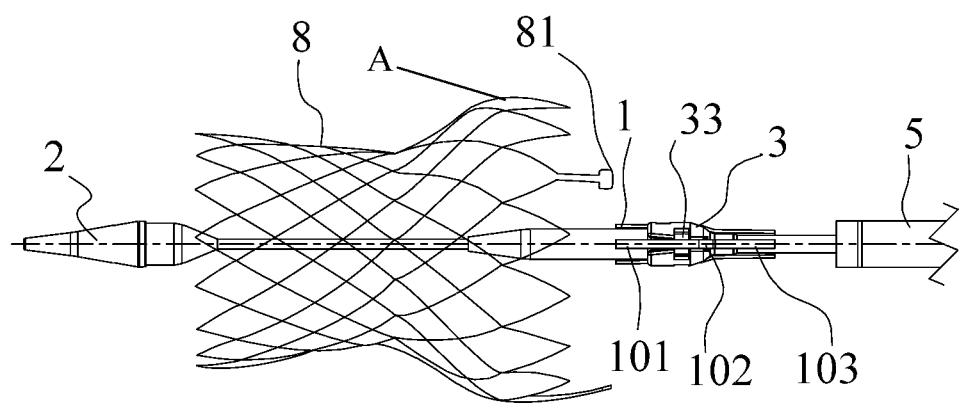
FIG. 7H shows a schematic structural view of the implantable instrument in a released configuration.

Referring to FIGS. 7F, 7G and 7H, in another embodiment, in order to ensure that the movable limiting bars have a small dynamic friction factor, each movable limiting bar 1 is preferably made of PTFE material. Each movable limiting bar 1 in FIGS. 7F to 7H has a length of 15 mm, a width adapted to suit the width of the fixing head 3 for the stent, and a thickness of 0.5 mm. When the movable limiting bars are in a constrained condition, three movable limiting bars axially extend through respective positioning grooves and further to the distal ends thereof, respectively. The valve stent 8 includes three T-shaped connecting ears. In order to fit the shape of the connecting ear, the positioning groove axially extends through the fixing head 3 and forms as a cross groove. In order to ensure the constraint effect, the axial extending area of the positioning groove is completely closed by a respective movable limiting bar 1. In other words, the width of the movable limiting bar 1 corresponds to the width of the axial extending area. In the case where the axial extending area axially extends with unequal widths at different positions, the width of the movable limiting bar 1 should at least correspond to the narrowest area of the axial extending area to ensure that the movable limiting bar 1 can be received in the positioning groove in a partial or complete manner. The outer surface of the movable limiting bar 1 may slightly protrude from the outer periphery of the fixing head 3 to reduce friction between the outer periphery of the fixing head 3 and the inner wall of the outer sheath 5.

After the valve stent 8 is loaded into the delivery device, the movable limiting bars are received in the outer sheath 5 together with the valve stent 8 which is surrounded by the movable limiting bars. In other words, the implantable instrument has an unreleased configuration which is completely surrounded by the outer sheath, in which each movable limiting bar 1 is in a loaded configuration. During the release of the valve stent 8, as shown in FIG. 7F, the outer sheath 5 is withdrawn and slides along the movable limiting bars in the direction indicated by the arrow M, and in the meantime, the movable limiting bars are in a working state. When the connecting ears are located in the outer sheath 5, the movable limiting bars act on the connecting ears under the constraint of the outer sheath 5, thereby preventing the connecting ears from springing out.

As shown in FIG. 7G, the outer sheath 5 is further withdrawn in the direction indicated by the arrow M. The terminal end 101 of the movable limiting bar 1 at the distal end is free of the constraint of the outer sheath 5, while the extending section 102 and the connecting ear of the valve stent are still located in the outer sheath 5. The extending section 102 acts on the connecting ear 81, and thus the connecting ear 81 is free of the great expansion force from the expanding stent during release and firmly clamped in the positioning groove 33 of the fixing head 3 for the stent. In other words, the extending section 102 acts on the connecting ear 81 and provides a radial pressing force to the connecting ear 81 of the valve stent 81 so that the connecting ear of the valve stent is secured in a stable manner, and free of the great expansion force from the expanding stent during release, and thus firmly clamped in the positioning groove 33 of the fixing head 3 for the stent, thereby avoiding the risk of falling off the positioning portion of the fixing head and a subsequent undesired complete release.

In the case where the valve stent is released at an undesired position, the stent can be retracted in the opposite direction of arrow M by pushing the outer sheath 5 for re-release. Referring to FIG. 7H, if the valve stent is released at the desired position, the outer sheath 5 is further withdrawn in the direction of arrow M. The terminal end 101 and the extending end 102 of the movable limiting bar 1 are no longer constrained by the outer sheath 5, and they expand with the valve stent 8. At this time, the movable limiting bars are in a non-working state. That is, there is no force applied to the connecting ears so that the valve stent 8 can be completely released.

It should be noted that the working state here refers to that where each movable limiting bar 1 is in a loaded configuration. The non-working state refers to that each movable limiting bar 1 is in a released configuration, in which the force from the outer sheath through the movable limiting bars to the connecting portions of the implantable instrument is released after the implantable instrument is transformed into the released configuration. For example, when the implantable heart valve stent is released by withdrawing the outer sheath, the force from the outer sheath through the movable limiting bars to the connecting ears of the implantable heart valve stent is released; in the meantime, the connecting ears of the valve stent expand radially and fall off the positioning grooves.

During the release, if the valve stent is released at an undesired position, the valve stent 8 can be retracted into the outer sheath 5 in the opposite direction of arrow M by pushing the outer sheath 5 for retrieval and re-release.

Compared to the prior art, the valve stent here can be retracted in a stable manner, so that it can be retracted into the sheath for re-release or retrieval in the case where the valve stent is released at an undesired position during release. A stable retracting force is the key to retracting the valve stent into the outer sheath 5. Due to the movable limiting bars which serve as a spacer, the connecting ears can be received in the positioning grooves in a stable manner, and the valve stent can be retracted into the outer sheath with the movement of the outer sheath which provides a strong force to the valve stent.

It should be noted that, during release, even though the implantable instrument is exposed partially, i.e., the implantable instrument is in the partial released configuration, each movable limiting bar 1 is in a loaded configuration.

If the valve stent is released at the desired position, the outer sheath 5 is further withdrawn in the direction of arrow M and becomes the configuration shown in FIG. 7H. The terminal end 101 and the extending end 102 of the movable limiting bar 1 are no longer constrained by the outer sheath 5, and they expand with the valve stent 8. At this time, the movable limiting bars are in the released configurations. That is, there is no force applied to the connecting ears so that the valve stent 8 can be completely released. When the valve stent 8 is completely released, the radial pressing force from the movable limiting bars to the connecting ears is released with the withdrawal of the outer sheath 5, and the movable limiting bars would not obstruct the released valve stent, thereby avoiding a displacement of the valve stent.

Figure 8:
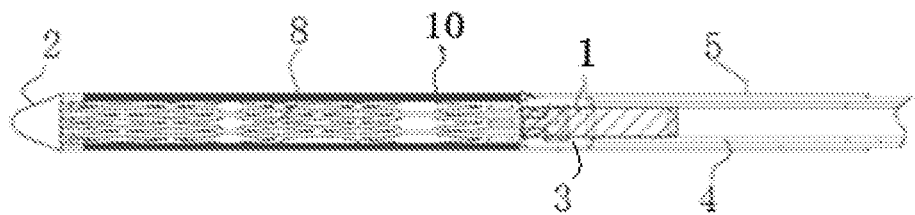
FIG. 8 shows a schematic structural view of a delivery device provided with fixing and guiding bars.
Figure 9:
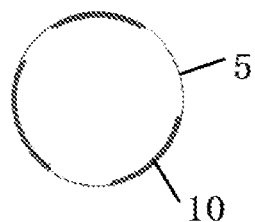
FIG. 9 is a cross sectional view of an outer sheath.
Figure 10:
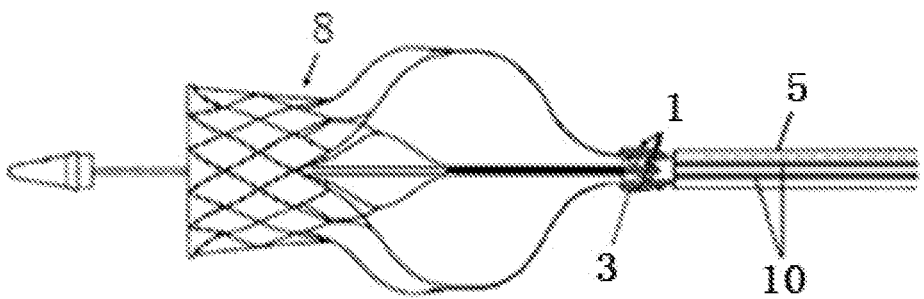
FIG. 10 shows a schematic structural view of the implantable instrument in a released configuration, in which the delivery device is provided with fixing and guiding bars and movable limiting bars.

Referring to FIGS. 8, 9 and 10, in other embodiments, the inner wall of the outer sheath 5 at the distal end is provided with at least one fixing and guiding bar 10.

Other than the movable limiting bar 1, the guiding head 2, the fixing head 3, the inner sheath 4, the outer sheath 5, and the valve stent 8 illustrated in the figures, the fixing and guiding bar 10 is also provided at the inner wall of the outer sheath 5. There are three fixing and guiding bars with the same length, which are evenly arranged in a spaced-apart manner in the circumferential direction and fixed on the inner surface of a tubular housing of the outer sheath 5 at the distal end, and provides smooth rails between the valve stent 8 and the outer sheath 5.

The fixing and guiding bars are alternatively arranged with the positioning grooves of the fixing head 3 (and thus the movable limiting bars) in the circumferential direction. When the valve stent 8 is constrained in the outer sheath 5, the proximal ends of the fixing and guiding bars abut against the fixing head 3, and are alternatively arranged with the positioning grooves one after the other.

The fixing and guiding bar 10 is a solid flat strip with a length of 10 mm to 80 mm, a width of 1 mm to 2 mm, and with a thickness of 0.2 mm to 0.5 mm. In this embodiment, the length of the fixing and guiding bar 10 corresponds to the axial length of the valve stent 8, and is designated to be about 60 mm.

The fixing and guiding bars may be fixed with the inner wall of the outer sheath 5 by bonding, binding, locking, or welding, or may be formed in one piece with the inner wall of the outer sheath 5. The fixing and guiding bars are made of PTFE material, and the portion thereof engaging with the implantable instrument 8 has a smooth surface or a lubricating coating. In a preferred implementation, the fixing and guiding bars are formed in one piece with the inner wall of the outer sheath 5, and the fixing and guiding bars are configured as ribs protruding from the inner surface of the outer sheath 5 with smooth surfaces or lubricating coatings.

The fixing and guiding bars may cooperate with various movable limiting bars which have a different length from the fixing and guiding bars such as the movable limiting bars with a length shown in FIGS. 1 and 2, or the short movable limiting bars shown in FIGS. 6 and 7A to 7H. In particular, FIG. 10 shows an implantable instrument in a released configuration in which movable limiting bars and fixing and guiding bars are provided. In order to clearly show the connecting ears of the valve stent 8 and the movable limiting bars, the outer sheath 5 shown in FIG. 10 is withdrawn until the movable limiting bars are completely exposed. The configuration shown in FIG. 10 is a momentary configuration which appears and disappears very quickly, and the connecting ears have not radially sprung out yet, but are ready to radially spring out.

Referring to FIG. 10, when the valve stent 8 is released, the outer sheath 5 contacts with and slides on the valve stent 8 through the fixing and guiding bar 10, so it can be withdrawn subject to a very small friction force so as to gradually release the stent.

When the outer sheath 5 is withdrawn to the position where the fixing head 3 is located, the valve stent 8 is only constrained in the outer sheath 5 at the connecting ears. At this time, the fixing and guiding bars completely fall off the valve stent 8, and the movable limiting bars press against the connecting ears under the constraint of the outer sheath 5. With a further withdrawal of the outer sheath 5, the constraint force from the movable limiting bars to the connecting ears gradually decreases, and the connecting ears are gradually released. In summary, the valve stent 8 is gradually released based on the smooth rails and the radial inward pressing force provided by the fixing and guiding bars and the movable limiting bars. Due to the fixing and guiding bars which provide smooth rails, and the movable limiting bars which fill the gap between adjacent fixing and guiding bars, the friction between the outer sheath 5 and the valve stent in the compressed configuration is reduced, which facilitates the release or retraction of the valve stent from or into the outer sheath.

In a further development, some of the movable limiting bars are provided on or in the positioning grooves of the fixing head and function to prevent the connecting ears of the stent from falling off the positioning grooves, the others are provided on the outer wall of the fixing head and serve as slide rails for the outer sheath sliding thereon. In a preferred implementation, the distal ends of the movable limiting bars corresponding to the positioning grooves are aligned with the fixing head, or do not extend beyond the most distal end of the fixing head, or slightly extend beyond the most distal end of the fixing head.

The following embodiments mainly describe the length and shape of the movable limiting bar 1 and the engagement for the connecting ears and the fixing head, and the other parts may refer to the above embodiments separately or in combination.

Figure 11A:
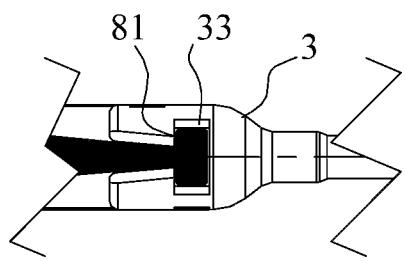
FIG. 11A illustrates the engagement between a connecting ear and a fixing head.
Figure 11B:
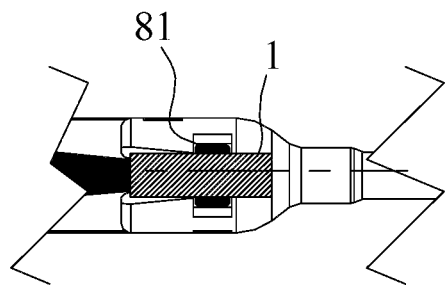
FIG. 11B shows the connecting ear illustrated in FIG. 11A, which is constrained by a movable limiting bar in a loaded condition.

Referring to FIGS. 11A and 11B, the connecting ear 81 is T-shaped, and the positioning portion of the fixing head 3 is configured as a positioning groove 33. In the loaded configuration, the connecting ear 81 is inserted in the positioning groove 33 that has a shape corresponding to the connecting ear 81. The movable limiting bar 1 is overlapped and pressed on the connecting ear 81 under the constraint of the outer sheath to prevent the connecting ear 81 from falling off the positioning groove 33. During the release of the stent, the constraint on the connecting ear 81 is not released until the outer sheath is completely separated from the movable limiting bar 1.

The positioning groove 33 has an appropriate depth that is no less than the thickness of the connecting ear which allows the connecting ear 81 to be radially inserted (received) in the positioning groove 33.

In other preferred embodiments, both the movable limiting bar 1 and the connecting ear 81 can be received in the positioning groove in an overlapping manner one on top of the other, and the positioning groove 33 has an appropriate depth which is equal to the sum of the thicknesses of the connecting ear and the movable limiting bar 1, so that the outer surface of the movable limiting bar 1 in the loaded configuration is aligned with the outer wall of the fixing head 3 in the radial direction.

Referring to FIGS. 12A to 12D, the connecting ear 81 is U-shaped. One side of the U-shaped opening is connected with the stent and closed. The positioning portion of the fixing head 3 is a positioning protrusion 34. The connecting ear 81 is extended around the positioning protrusion 34 with the U-shaped structure thereof to achieve its axial positioning. In order to prevent the connecting ear 81 from radially protruding too much, a recess 35 is provided around the outer periphery of the positioning protrusion 34, i.e., on the outer wall of the fixing head 3. The connecting ear 81 is received in the recess 35 in such a manner that the outer surface of the connecting ear 81 is aligned with the outer wall of the fixing head 3 in the radial direction.

In other preferred embodiments, both the movable limiting bar 1 and the connecting ear 81 can be received in the recess 35 in an overlapping manner one on top of the other, and the recess 35 has an appropriate depth which is equal to the sum of the thicknesses of the connecting ear and the movable limiting bar 1, so that the outer surface of the movable limiting bar 1 in the loaded configuration is aligned with the outer wall of the fixing head 3 in the radial direction.

Figure 12A:
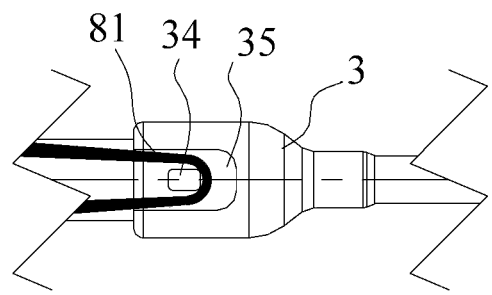
FIG. 12A illustrates the engagement between another connecting ear and another fixing head.
Figure 12B:
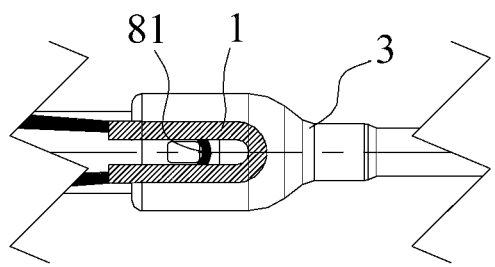
FIGS. 12B to 12D show the connecting ear illustrated in FIG. 12A which is constrained by various movable limiting bars with different shapes in a loaded condition.

Referring to FIG. 12B, the movable limiting bar 1 has a branched structure which is U-shaped, with the branches extending towards the distal end and overlapping on the outer side of the connecting ear 81, and the connection portion of the branches fixed on the outer side of the fixing head 3.

Figure 12C:
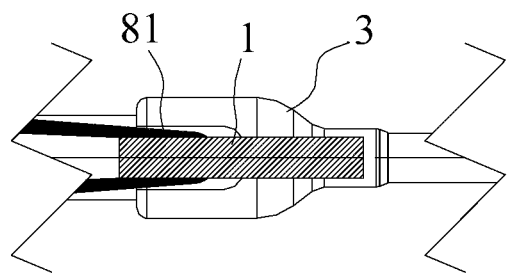

Referring to FIG. 12C, the movable limiting bar 1 is configured as a single strip, and also extends towards the distal end and overlaps the outer side of the connecting ear 81.

Figure 12D:
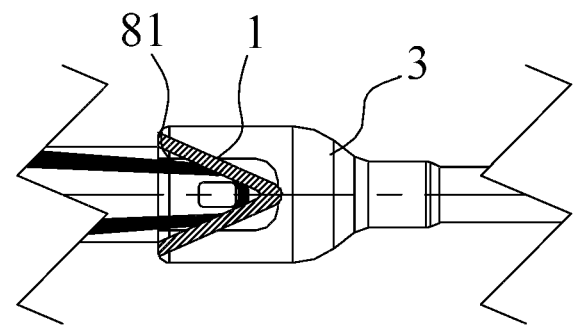

Referring to FIG. 12D, the movable limiting bar 1 has a branched structure which is V-shaped or Y-shaped, with the branches extending towards the distal end and overlapping the outer side of the connecting ear 81, and the connection portion of the branches fixed on the outer side of the fixing head 3.

FIGS. 13A to 13D illustrate configurations in which the connecting ear is pressed by various movable limiting bars with different lengths. In the loaded state of the implantable heart valve stent, the movable limiting bar 1 is constrained by the outer sheath 5 and positions the connecting ear 81 on the outer side of the fixing head. The positioning protrusion 34 is shown as an example of the positioning portion of the fixing head, and at least a part of the distal end of the movable limiting bar 1 overlaps and presses on the connecting ear 81.

Figure 13A:
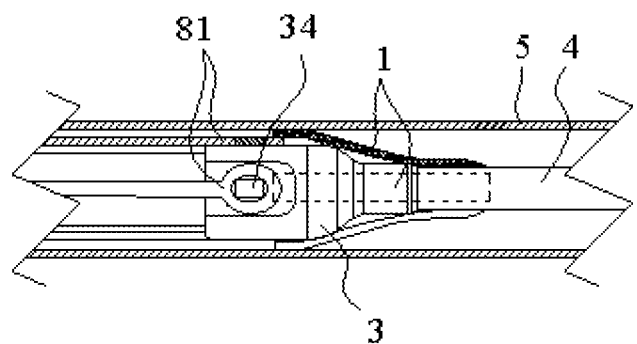
FIGS. 13A to 13D show a further connecting ear which is constrained by various movable limiting bars with different lengths.

Referring to FIG. 13A, the distal end of the movable limiting bar 1 overlaps and presses on the connecting ear 81, and does not extend to the positioning protrusion 34. The distal end of the movable limiting bar 1 only overlaps and presses on a small area of the connecting ear 81.

Figure 13B:
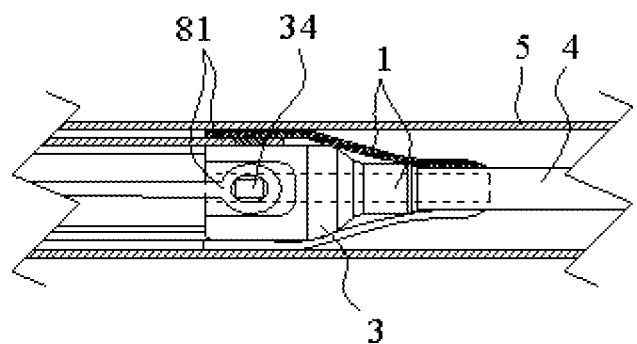

Referring to FIG. 13B, the distal end of the movable limiting bar 1 overlaps and presses on the connecting ear 81, and at least axially extends to completely cover the positioning portion of the fixing head. In other words, the distal end of the movable limiting bar 1 extends beyond the positioning protrusion 34 to the distal end of the fixing head 3. The axial distal end of the movable limiting bar 1 overlaps and presses on the connecting ear 81 and the entire fixing head 3.

Figure 13C:
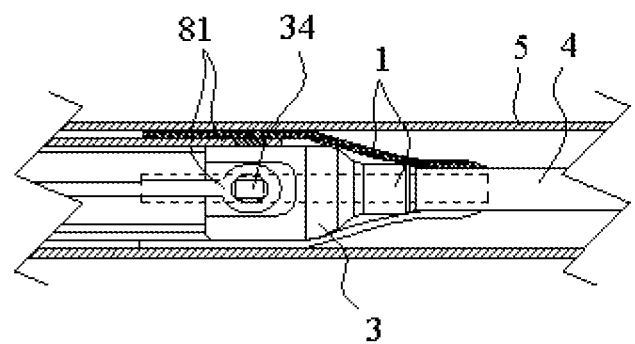

Referring to FIG. 13C, the distal end of the movable limiting bar 1 overlaps and presses on the connecting ear 81. The distal end of the movable limiting bar 1 axially extends beyond the fixing head.

Figure 13D:
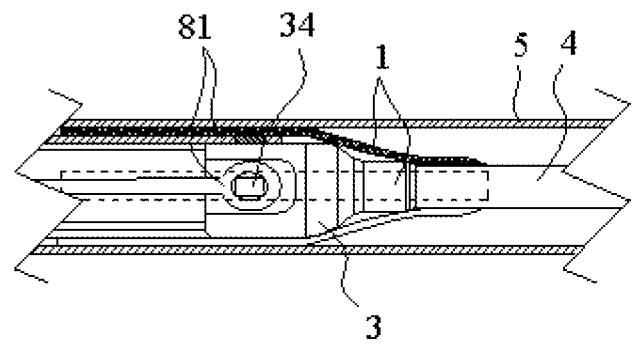

Referring to FIG. 13D, the distal end of the movable limiting bar 1 overlaps and presses on the connecting ear 81. The distal end of the movable limiting bar 1 axially extends beyond the fixing head to the portion of the implantable heart valve stent with the greatest diameter. Considering that the outer diameter of the implantable heart valve stent in the loaded configuration remains substantially unchanged due to the constraint of the outer sheath, the portion of the implantable heart valve stent with the greatest diameter may be regarded as the portion of the released implantable heart valve stent with the greatest diameter.

The embodiments are described taking the heart valve stent as an example of the implantable instrument. It would be appreciated for a person skilled in the art that other implantable instruments can also be delivered into the corresponding sites of the human body by the delivery device disclosed here.

The features described in the above various embodiments may be combined. In order to simplify the descriptions, not all possible combinations of the features in the above embodiments have been described. However, any combinations of the features should be within the scope of the disclosure as long as no conflict resides between these features.

The above embodiments are only several implementations of the present disclosure which are described specifically and in detail, without limitation to the scope claimed by the present disclosure. Those skilled in the art can make various modifications and variations to the embodiments without departing from the spirit and scope of the present disclosure. Obviously, these modifications and variations should fall into the scope claimed by the present disclosure. Therefore, the scope of the disclosure shall be subject to the appended claims.

What is claimed is:

1. An assembly, comprising:
an implantable instrument having a main body which has an outer periphery and at least one connecting ear which is connected with the main body; and
a delivery device separate from the implantable instrument and facilitating control of the implantable instrument, comprising:
a core tube having a distal end and a proximal end,
a guiding head which is fixed at the distal end of the core tube,
a fixing head which is fixed on the core tube and is provided with at least one positioning portion on an outer wall thereof for engaging with the at least one connecting ear of the implantable instrument, and the positioning portion is configured as a positioning groove axially extending through the fixing head, wherein the proximal end of the core tube extends through and out of the fixing head, and wherein at least a part of the main body of the implantable instrument is positioned between the guiding head and the fixing head,
an outer sheath which is configured for surrounding the outer periphery of the main body of the implantable instrument and is slidable in an axial direction, and
at least one movable limiting bar having a proximal end being a starting end which is fixed with at least one of the core tube and the fixing head, and a distal end being a terminal end which is configured between the implantable instrument and the outer sheath and is movable, wherein,
the at least one movable limiting bar is configured to maintain the engagement between the at least one connecting ear and the at least one positioning portion under the constraint of the outer sheath when the implantable instrument is in a loaded configuration.

2. The assembly of claim 1, wherein when the implantable instrument assumes the loaded configuration, the connecting ear is configured to be inserted in a respective positioning groove, and the movable limiting bar is configured to overlap and abut against an outer side of a respective connecting ear to maintain the engagement between the connecting ear and the positioning portion.

3. The assembly of claim 2, wherein the number of the at least one movable limiting bar is the same as that of the at least one positioning groove, and the at least one movable limiting bar corresponds to the at least one positioning groove respectively in a circumferential direction.

4. The assembly of claim 1, wherein the most distal end of the movable limiting bar is aligned with the most distal end of the fixing head, or extends no more than the most distal end of the fixing head, or extends slightly beyond the most distal end of the fixing head.

5. The assembly of claim 2, wherein a portion of the movable limiting bar for engaging with the positioning groove is configured to be partially or completely received in the positioning groove.

6. The assembly of claim 5, wherein an area of the positioning groove that axially extends through the fixing head is configured to be closed by the movable limiting bar.

7. The assembly of claim 2, wherein a portion of the movable limiting bar that is configured to be received in the positioning groove contacts with or abuts radially and inwardly against the connecting ear.

8. The assembly of claim 5, wherein the movable limiting bar is configured to be aligned with or protrude from the outer wall of the fixing head in a radial direction.

9. The assembly of claim 1, wherein the at least one movable limiting bar comprises two, three, or four movable limiting bars that are evenly arranged in a circumferential direction.

10. The assembly of claim 1, wherein the movable limiting bar has a hollow or a solid structure.

11. The assembly of claim 10, wherein the movable limiting bar is configured as a flat strip with a solid structure.

12. The assembly of claim 1, wherein at least one of a portion of the movable limiting bar for engaging with the sheath and a portion of the movable limiting bar for engaging with the implantable instrument has a smooth surface and/or a lubricious coating.

13. The assembly of claim 1, wherein the movable limiting bar is made of PTFE material.

14. The assembly of claim 1, wherein the loaded configuration of the implantable instrument comprises an unreleased configuration, in which the implantable instrument is completely surrounded by the outer sheath, and a partial released configuration, in which the implantable instrument is partially exposed;

when the implantable instrument is in the loaded configuration, the at least one movable limiting bar is configured to maintain the engagement between the at least one connecting ear of the implantable instrument and the at least one positioning portion under the constraint of the outer sheath so as to prevent the at least one connecting ear from falling off the fixing head; and when the implantable instrument is in a released configuration in which the implantable instrument is completely exposed out of the outer sheath, the force applied by the at least one movable limiting bar to maintain the engagement between the at least one connecting ear and the at least one positioning portion is released so as to allow the at least one connecting ear of the implantable instrument to fall off the at least one positioning portion.

15. The assembly of claim 14, wherein when the implantable instrument is in the loaded configuration, a radial outer side of the movable limiting bar abuts against an inner wall of the sheath, a radial inner side of the movable limiting bar abuts against the connecting ear, and a portion of the at least one movable limiting bar that contacts with the at least one connecting ear of the implantable instrument is located at a radial outer side of the implantable instrument.

16. The assembly of claim 1, wherein the movable limiting bar is configured as a single strip, or a branched structure, wherein branches of the branched structure extend towards the distal end to overlap and abut against an outer side of the connecting ear, and a connection of the branched structure connecting the branches is fixed at an outer side of the fixing head.

\* \* \* \* \*